United States Patent
Woo et al.

(10) Patent No.: US 11,185,247 B2
(45) Date of Patent: Nov. 30, 2021

(54) BODY FAT MEASUREMENT APPARATUS AND METHOD

(71) Applicant: BiLab Co., Ltd., Seoul (KR)

(72) Inventors: Eung Je Woo, Seongnam-si (KR); Tong In Oh, Suwon-si (KR)

(73) Assignee: BiLab Co., Ltd., Seoul (KR)

(*) Notice: Subject to any disclaimer, the term of this patent is extended or adjusted under 35 U.S.C. 154(b) by 286 days.

(21) Appl. No.: 16/082,566

(22) PCT Filed: Mar. 15, 2017

(86) PCT No.: PCT/KR2017/002809
§ 371 (c)(1),
(2) Date: Sep. 6, 2018

(87) PCT Pub. No.: WO2017/160084
PCT Pub. Date: Sep. 21, 2017

(65) Prior Publication Data
US 2019/0038175 A1 Feb. 7, 2019

(30) Foreign Application Priority Data
Mar. 17, 2016 (KR) .................. 10-2016-0032396

(51) Int. Cl.
*A61B 5/053* (2021.01)
*A61B 5/00* (2006.01)
(Continued)

(52) U.S. Cl.
CPC .......... *A61B 5/0537* (2013.01); *A61B 5/0064* (2013.01); *A61B 5/0077* (2013.01);
(Continued)

(58) Field of Classification Search
CPC ... A61B 5/0064; A61B 5/0077; A61B 5/0536; A61B 5/0537; A61B 5/1073; A61B 5/4872; A61B 5/6823; A61B 5/6831
See application file for complete search history.

(56) References Cited

U.S. PATENT DOCUMENTS

2004/0077969 A1* 4/2004 Onda .................. A61B 5/4872
600/547
2004/0131997 A1* 7/2004 McGuire ............ G09B 19/0092
434/127
(Continued)

FOREIGN PATENT DOCUMENTS

KR 10-1079462 B1 11/2011
KR 10-1324704 B1 11/2013

OTHER PUBLICATIONS

International Search Report of PCT/KR2017/002809 dated May 30, 2017.

*Primary Examiner* — Jennifer Pitrak McDonald
*Assistant Examiner* — Pamela M. Bays
(74) *Attorney, Agent, or Firm* — Sughrue Mion, PLLC (57) ABSTRACT

A body fat measurement apparatus, according to the present invention, comprises: an electrode unit which has a plurality of electrodes and can be worn around the body of the subject to be measured; a first measurement unit which is for obtaining a three-dimensional image of the subject's body part to be measured; a second measurement unit which is for measuring the impedance by means of injecting a current into the electrodes; and a control unit which is for restoring the conductivity and permittivity images of the subject by means of the three-dimensional image and the impedance value and thus separately calculating the amount of subcutaneous fat and visceral fat. According to the present inven-
(Continued)

tion, measurement accuracy of the subcutaneous fat and visceral fat can be improved even at a low cost.

6 Claims, 10 Drawing Sheets

(51) Int. Cl.
    *A61B 5/0537*     (2021.01)
    *A61B 5/0536*     (2021.01)
    *A61B 5/107*     (2006.01)
    *G16H 30/40*     (2018.01)

(52) U.S. Cl.
    CPC .......... *A61B 5/0536* (2013.01); *A61B 5/4872* (2013.01); *A61B 5/6823* (2013.01); *A61B 5/6831* (2013.01); *A61B 5/002* (2013.01); *A61B 5/1073* (2013.01); *A61B 5/1075* (2013.01); *A61B 5/1077* (2013.01); *A61B 5/1079* (2013.01); *A61B 5/6801* (2013.01); *A61B 2560/0468* (2013.01); *A61B 2576/02* (2013.01); *G16H 30/40* (2018.01)

(56) References Cited

U.S. PATENT DOCUMENTS

| | | | |
|---|---|---|---|
| 2006/0085049 A1* | 4/2006 | Cory | A61B 5/0536 607/48 |
| 2007/0038140 A1* | 2/2007 | Masuo | A61B 5/0537 600/547 |
| 2009/0182243 A1* | 7/2009 | Oku | A61B 5/4872 600/547 |
| 2010/0198101 A1* | 8/2010 | Song | A61N 5/1049 600/547 |
| 2010/0312143 A1* | 12/2010 | Kim | A61B 5/4869 600/587 |
| 2011/0295144 A1* | 12/2011 | Murakawa | A61B 5/4872 600/547 |
| 2013/0041235 A1* | 2/2013 | Rogers | A61B 5/1107 600/306 |
| 2016/0100791 A1* | 4/2016 | Arad (Abboud) | A61B 5/6831 600/547 |

\* cited by examiner

BODY FAT MEASUREMENT APPARATUS AND METHOD

TECHNICAL FIELD

Example embodiments relate to a body fat measurement apparatus and method, and more particularly, to a body fat measurement apparatus and method that may separately measure and visualize subcutaneous fat and visceral fat of a human body.

RELATED ART

Body fat includes subcutaneous fat that is present between the derma and the fascia and visceral fat that is present between internal organs inward the abdominal cavity. The subcutaneous fat functions to store and synthesize nutrients, to block heat, and to absorb a shock, and the visceral fat melts in the blood and secretes a material harmful to a human body, which may lead to arteriosclerosis, diabetes, heart disease, hypertension, and the like. Due to such a difference in health effect between the subcutaneous fat and the visceral fat, there is a need to accurately measure subcutaneous fat and the visceral fat.

In the meantime, in view of diagnosing obesity, it is important to separately measure abdominal subcutaneous fat and visceral fat. For this purpose, an imaging device, for example, X-ray computed tomography (CT), magnetic resonance imaging (MRI), and the like, may be used. However, a medical imaging device, such as X-ray CT and MRI, may not be used for a regular body fat measurement due to high examination cost. Accordingly, in recent years, research on a technique capable of accurately measuring body fat including visceral fat at low cost is continuously conducted.

DISCLOSURE OF THE INVENTION

Technical Goals

Example embodiments are conceived to outperform the aforementioned issues and provide a body fat measurement apparatus and method that may numerically calculate an amount of subcutaneous fat and an amount of visceral fat and may output calculation results with an image.

Solutions

According to an example embodiment, there is provided a body fat measurement apparatus including an electronic unit having a plurality of electrodes and configured to be attachable or wearable around a body of a subject to be measured; a first measurement unit configured to obtain a three-dimensional (3D) image for a measurement target part of the subject; a second measurement unit configured to measure an impedance value by injecting current into the electrode; and a control unit configured to restore conductivity and permittivity images of the subject using the 3D image and the impedance value and to separately calculate an amount of subcutaneous fat and an amount of visceral fat.

According to an aspect, the plurality of electrodes may use at least one of a simple electrode and a composite electrode, and the electrode unit may include an electrode belt having a plurality of electrode installation holes via which the plurality of electrodes is installed, respectively, and made of an elastic material.

According to an aspect, the electrode belt may have a contact surface on which the plurality of electrodes is installed and configured to contact with the subject and an exposed surface configured to face the contact surface, exposed toward the first measurement unit, and on which a plurality of displays formed using a plurality of colors and patterns is provided to correspond to the plurality of electrodes, respectively.

According to an aspect, the first measurement unit may include a photographing unit configured to obtain a 3D image by taking a photo of the display of the electrode unit mounted to the subject; a photographing support configured to ascend or descend with supporting the photographing unit or to be rotatable based on the subject; and a rotator configured to be rotatable with supporting the subject and to adjust a distance between the photographing unit and the subject.

According to an aspect, the second measurement unit may include a cable belt configured to connect to the plurality of electrodes; and an impedance measurer configured to measure voltage induced by the current injected into the electrode and to transmit the measured voltage to the control unit through the cable belt.

According to an aspect, the control unit may be configured to calculate a circumference of the measurement target part of the subject and a location of a selected electrode in response to completion of the 3D image for the measurement target part of the subject using the first measurement unit, and restore the conductivity and permittivity images of the measurement target part using the impedance value measured from the second measurement unit and separately calculate the amount of subcutaneous fat and the amount of visceral fat in the restored image.

According to an example embodiment, there is provided a method of measuring body fat, the method including providing an electrode belt having a plurality of electrodes along a circumference of a measurement target part of a subject; obtaining a 3D image by taking a photograph of a display provided on each of the plurality of electrodes of the electrode belt; calculating the circumference of the measurement target part of the subject and a location of a selected electrode; measuring an impedance value by connecting a cable belt for injecting current to the electrode belt; restoring conductivity and permittivity images of the measurement target part of the subject using the impedance value; and separately calculating an amount of subcutaneous fat and an amount of visceral fat of the measurement target part of the subject.

According to an aspect, the plurality of electrodes may use at least one of a simple electrode and a composite electrode.

According to an aspect, the electrode belt may have a contact surface on which the plurality of electrodes is installed and configured to contact with the subject and an exposed surface configured to face the contact surface, exposed toward the first measurement unit, and on which a plurality of displays formed using a plurality of colors and patterns is provided to correspond to the plurality of electrodes, respectively. The electrode belt may be made of an elastic material.

According to an aspect, a photographing unit may be provided to obtain a 3D image by taking a photo of the display of the electrode unit mounted to the subject, and the photographing unit may be configured to ascend or descend or to be rotatable based on the subject, and the subject may be rotatably supported by a rotatable rotator.

Effect

According to example embodiments, first, since it is possible to accurately measure body fat by separating the body fat into subcutaneous fat and visceral fat, it is possible to enhance the reliability of a subject through an enhancement of measurement accuracy.

Second, since it is possible to separately measure an amount of subcutaneous fat and an amount of visceral fat using a three-dimensional (3D) image and an impedance value, it is possible to perform accurate measurement at low cost.

BEST MODE

Hereinafter, example embodiments are described with reference to the accompanying drawings.

Figure 1:
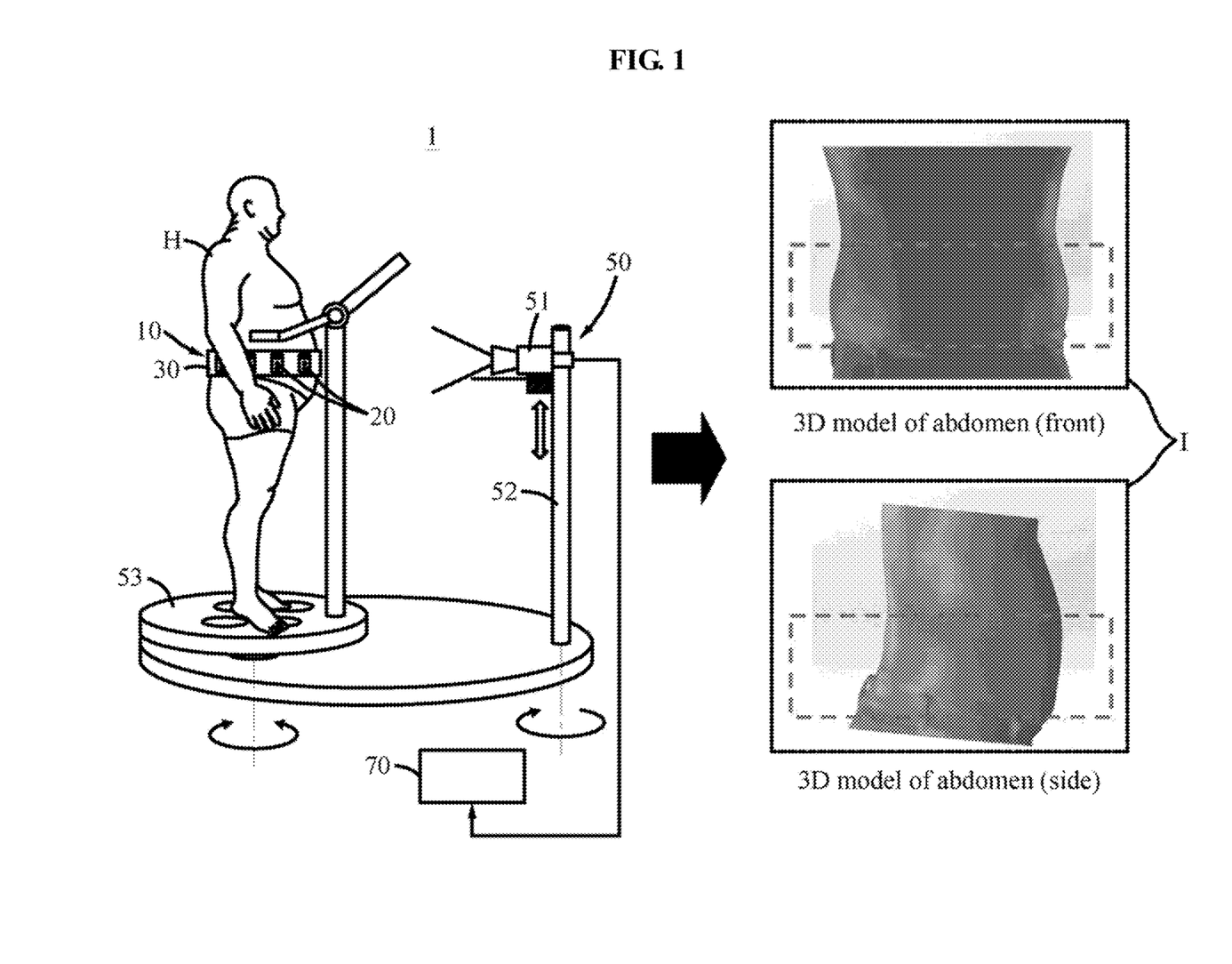
FIG. 1 illustrates a body fat measurement apparatus according to a first example embodiment.
Figure 2:
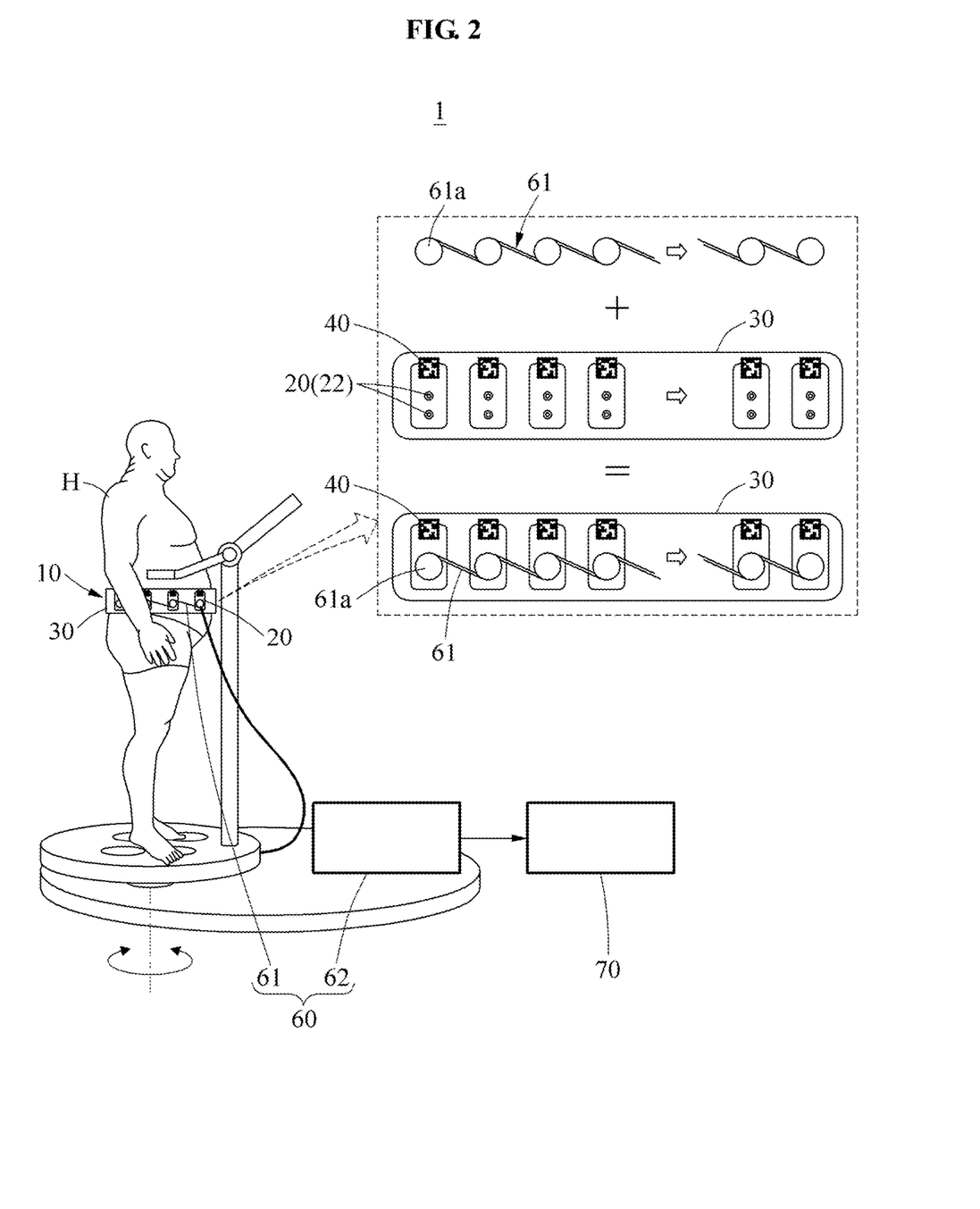
FIG. 2 illustrates a state in which a cable belt is provided to the body fat measurement apparatus of FIG. 1.

Referring to FIGS. 1 and 2, a body fat measurement apparatus 1 according to an example embodiment includes an electrode unit 10, a first measurement unit 50, a second measurement unit 60, and a control unit 70.

The electrode unit 10 may include a plurality of electrodes 20 and may be provided around a circumference of a body of a subject H to be measured. To this end, the electrode unit 10 includes an electrode belt 30 to which the plurality of electrodes 20 is provided.

Figure 3A:
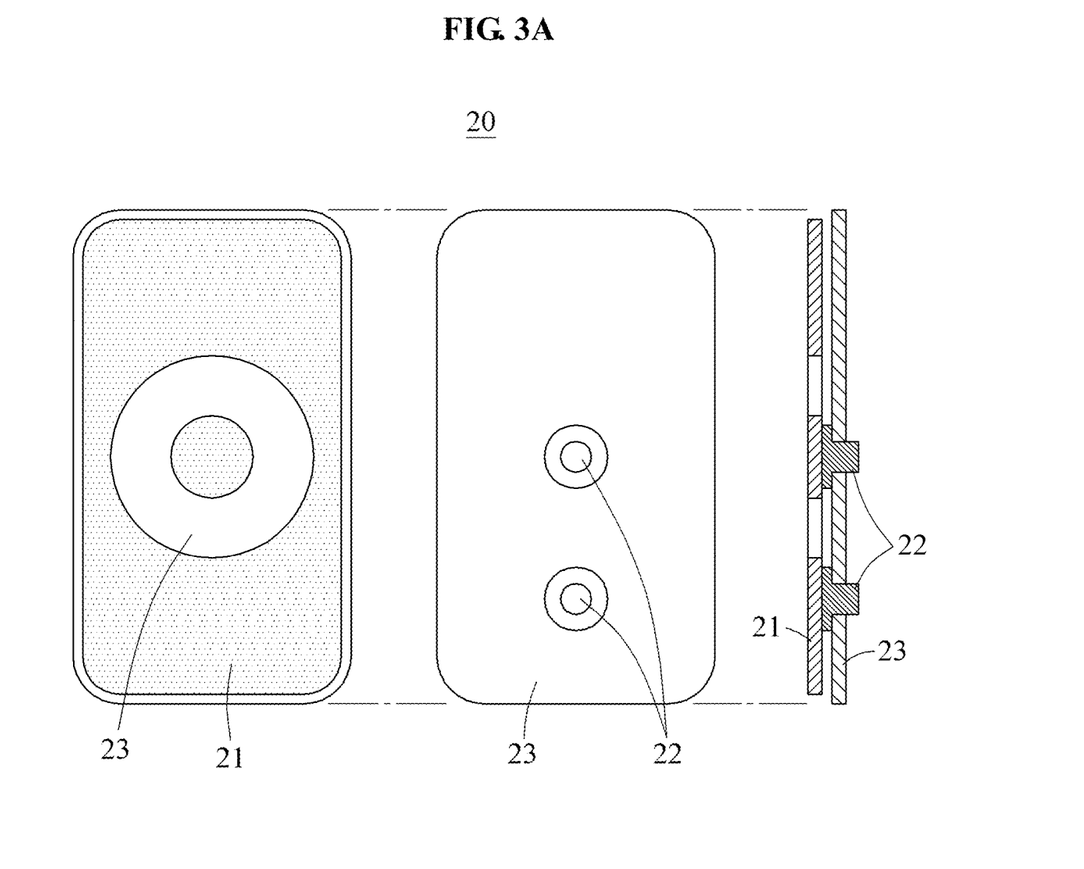
FIG. 3A illustrates a composite electrode used for the body fat measurement apparatus of FIG. 1.

Referring to FIG. 3A, the plurality of electrodes 20 may include a composite electrode 20. Hereinafter, the electrode 20 may also be referred to as a composite electrode. The composite electrode 20 includes a first electrode 21 configured to inject current and made of a conductive material and a second electrode 22 configured to measure voltage and made of a conductive material. The first electrode 21 may inject the current with a relatively large area compared to that of the second electrode 22. A single pair of second electrodes 22 are provided to measure the voltage with a relatively small area compared to that of the first electrode 21.

Here, the first electrode 21 is in a planar shape and the single pair of second electrodes 22 each is configured to connect to the first electrode 21 and is in a protruding shape. The first and second electrodes 21 and 22 of each of the plurality of composite electrodes 20 are provided to the electrode belt 30 based on a nonconductor 23 made of a nonconductive material.

Figure 3B:
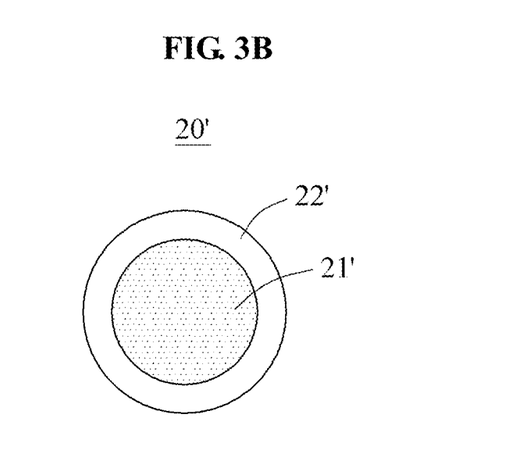
FIG. 3B illustrates an example of a simple electrode.

In the meantime, although it is illustrated that the electrode 20 includes the composite electrode, it is provided as an example only. Referring to FIG. 3B, the electrode 20 may include a simple electrode 20' as a modified example. In the case of the simple electrode 20', injection of current or measurement of voltage may be performed using a single conductive electrode 21' and the simple electrode 20' is supported by a nonconductor 22'.

Figure 4A:
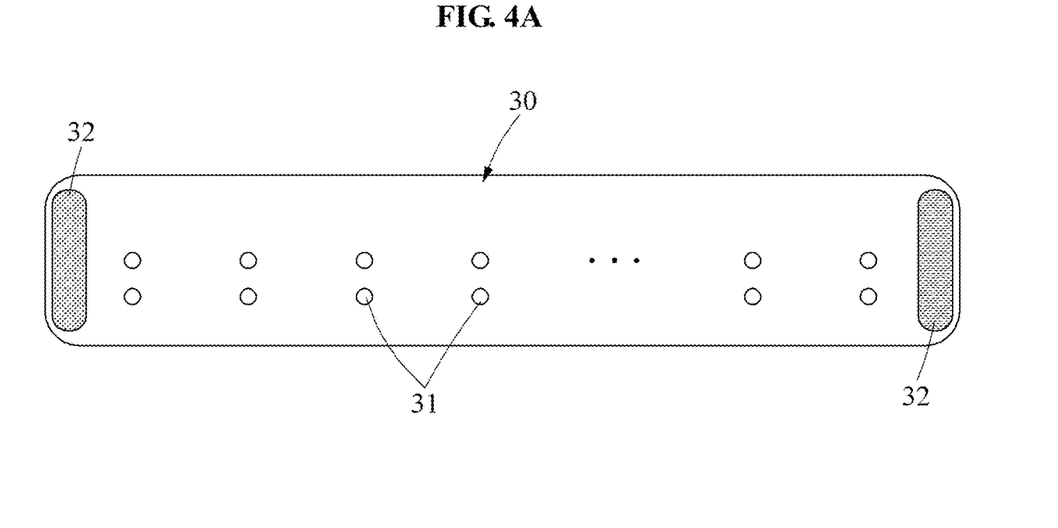
FIG. 4A is a plane view illustrating an electrode belt.

Referring to FIG. 4A, the electrode belt 30 includes a plurality of electrode installation holes 31 via which the plurality of composite electrodes 20 is fixable. The plurality of electrodes installation holes 31 is provided to correspond to a single pair of protruding second electrodes 22.

The electrode belt 30 may be formed using an elastic material, for example, a fiber and a polymer compound such as silicone. A number of the plurality of electrodes installation holes 31 and a number of the composite electrodes 20 that are provided to the electrode belt 30 may be modified. A single pair of fasteners 32 configured to couple with each other are provided at both ends of the electrode belt 30, respectively, to maintain a state in which the electrode belt 30 is worn around the circumference of the body of the subject H.

In the example embodiment, the electrode belt 30 is worn around an abdominal circumference that is a measurement target part of the subject H and is fastened by way of the Velcro-typed fasteners 32 provided at both ends. However, it is provided as an example only. The fastener 32 may use various types of fixing devices, such as a hook type.

Figure 4B:
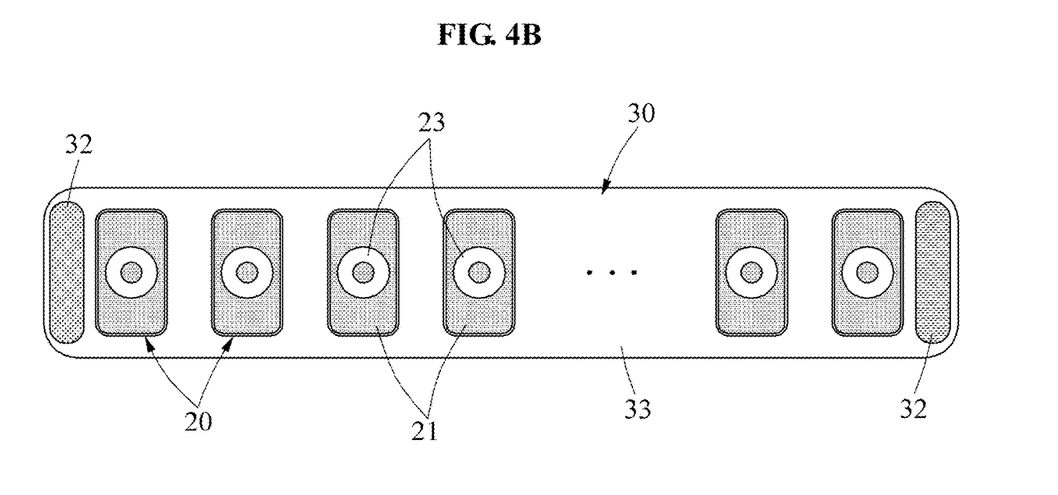
FIG. 4B illustrates a state in which a composite electrode is provided on a contact surface of an electrode belt.
Figure 4C:
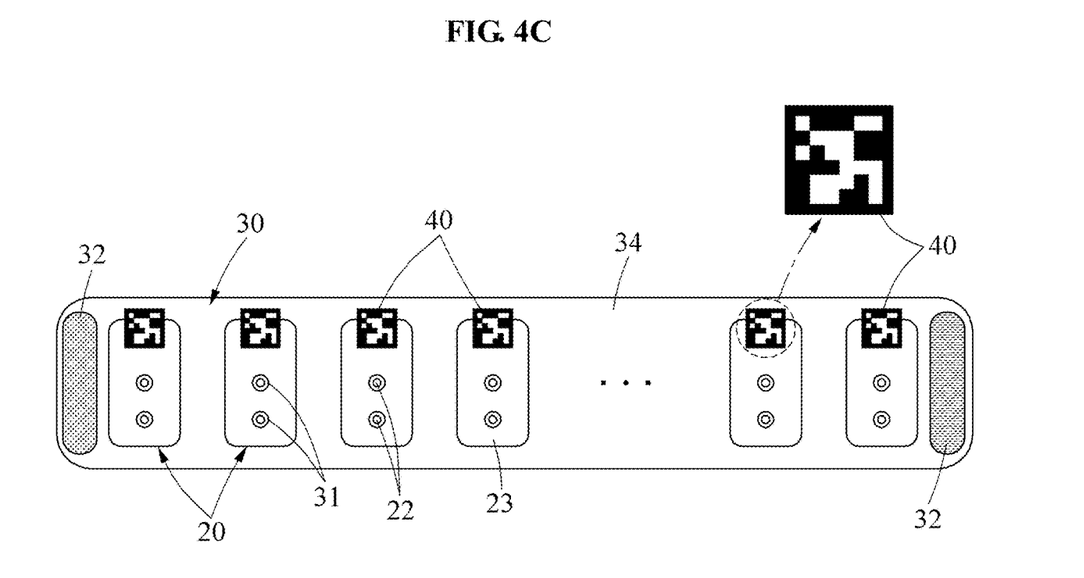
FIG. 4C illustrates a state in which a composite electrode and a display are provided on an exposed surface of an electrode belt.

The electrode belt 30 includes a contact surface 33 on which the plurality of composite electrodes 20 is installed and configured to contact with the subject H as illustrated in FIG. 4B, and an exposed surface 34 configured to face the contact surface 33 as illustrated in FIG. 4C and exposed toward the first measurement unit 50 to be described below. Here, the first electrode 21 of the composite electrode 20 is exposed on the contact surface 33 of the electrode belt 30 and the second electrode 22 is exposed on the exposed surface 34 via the electrode installation hole 31. In addition, a plurality of displays 40 (e.g., markers) formed using a plurality of colors and patterns corresponding to information associated with the plurality of composite electrodes 20, respectively, is provided to correspond to the plurality of composite electrodes 20, respectively, on the exposed surface 34 of the electrode belt 30.

The first measurement unit 50 may obtain a three-dimensional (3D) image I used to calculate the circumference of the measurement target part of the subject H and a location of the composite electrode 20. The first measurement unit 50 includes a photographing unit 51, a photographing support 52, and a rotator 53.

The photographing unit 51 may obtain the 3D image I by taking a photo of the display 40 of the electrode unit 10 mounted to the subject H. The photographing unit 51 includes a 3D camera capable of measuring 3D coordinates with a laser pointer and a light emitting diode (LED) lighting. As shown in images I of FIG. 1, the photographing unit 51 outputs a 3D model image I of abdomen that is a part around which the subject H wears the electrode belt 30. In detail, the photographing unit 51 may obtain 3D volume information of the abdomen that is the measurement target part of the subject H from information associated with two-dimensional (2D) images including the displays 40 formed using a plurality of colors and patterns and of which actual sizes are known.

The photographing support 52 may ascend or descend with supporting the photographing unit 51 or may rotate based on the subject H. That is, the photographing support 52 may adjust a photographing location with supporting the photographing unit 51.

The rotator 53 may rotate with supporting the subject H, and may adjust a distance between the photographing unit 51 and the subject H. Herein, the rotator 53 is illustrated as an example to include a rotating disk that is rotatable with supporting the subject H.

Figure 5A:
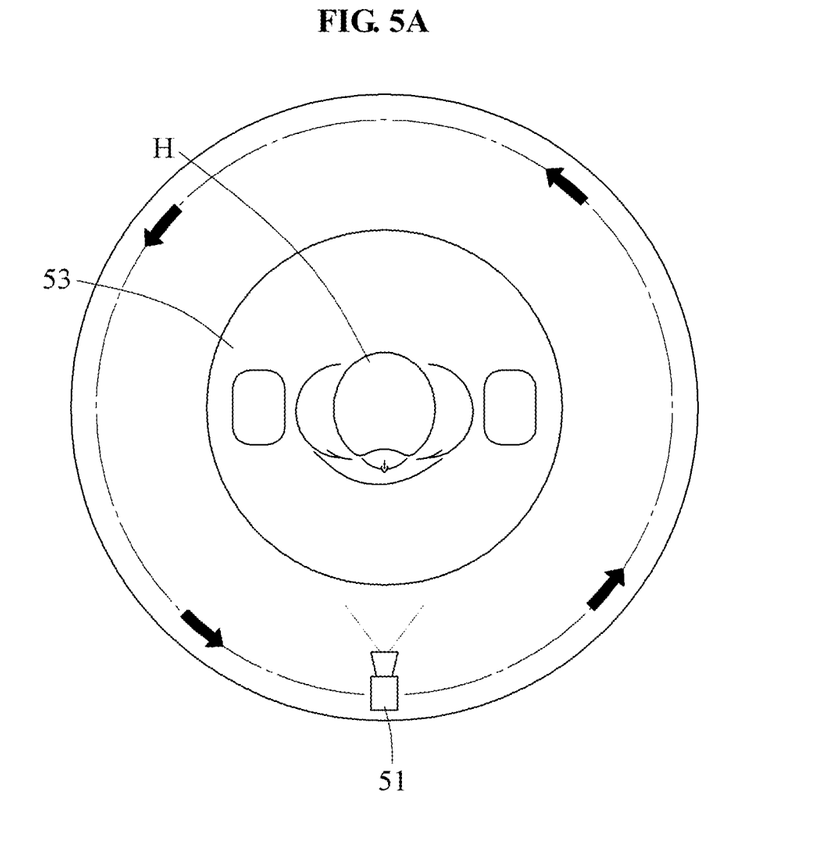
FIG. 5A illustrates an example of photographing a three-dimensional (3D) image with rotating of a photographing support.
Figure 5B:
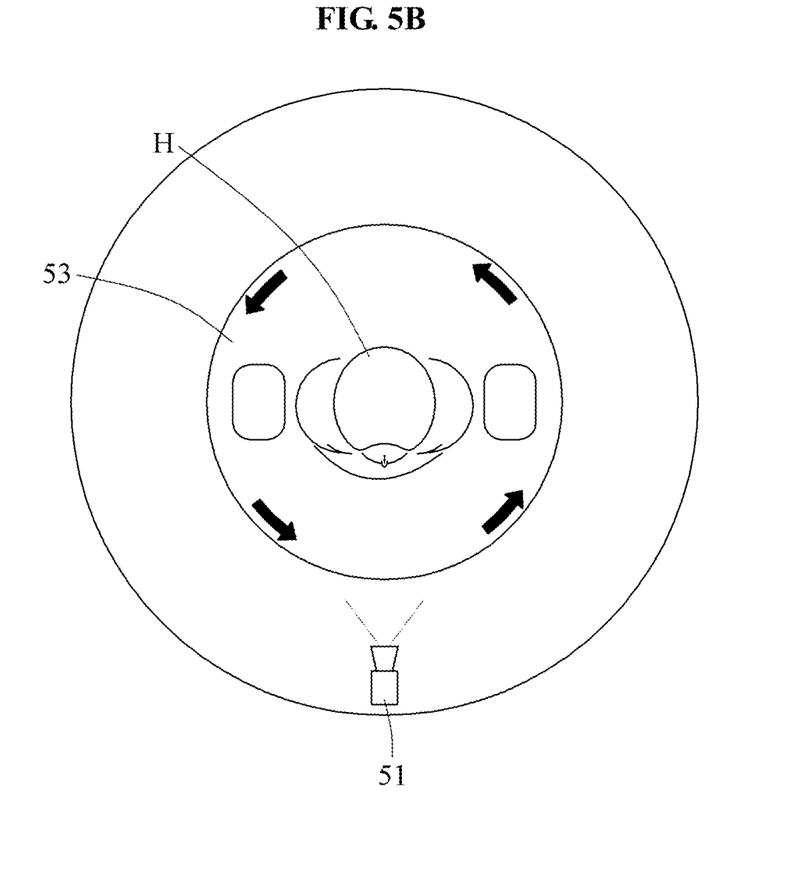
FIG. 5B illustrates an example of photographing a 3D image with rotating of a rotator.

Due to the photographing support 52 and the rotator 53 constructed as above, the photographing unit 51 may obtain a 3D modeling image in such a manner that, in response to rotating of the photographing support 52, the photographing unit 51 rotates based on the subject H as illustrated in FIG. 5A, or the rotator 53 supporting the subject H rotates as illustrated in FIG. 5B.

The second measurement unit 60 my measure an impedance value through the electrode 20 that is calculated and selected by the first measurement unit 50. The second measurement unit 60 includes a cable belt 61 and an impedance measurer 62.

The cable belt 61 is connected to the second electrodes 22 exposed via the electrode installation holes 31 via which the plurality of composite electrodes 20 is fastened. Here, the cable belt 61 includes a plurality of connecting cable terminals 61a corresponding to the plurality of composite electrodes 20 and configured to inject current.

The impedance measurer 62 may measure voltage induced by the current injected into the composite electrode 20 through the cable belt 61. In detail, the impedance measurer 62 may generate multi-frequency current through the cable belt 61 and may apply the current to the composite electrodes 20 of the electrode belt 30 mounted to the subject H while controlling a magnitude and a phase. Here, the multi-frequency current may be injected through the first electrode 21 of the composite electrode 20 and a voltage difference signal induced by the injected current may be obtained using the second electrode 22 of the composite electrode 20.

The control unit 70 may calculate the circumference of the measurement target of the subject H and an electrode location from the 3D image I that is obtained from the first measurement unit 50, may restore conductivity and permittivity images of the subject H based on the impedance value measured through the second measurement unit 60, and may separately calculate an amount of subcutaneous fat and an amount of visceral fat.

In detail, the control unit 70 may control a sensitivity and a resolution according to locations of the plurality of composite electrodes 20 based on measurement protocols of the plurality of composite electrodes 20 to visualize tissue characteristics including location information of subcutaneous fat and visceral fat of the subject H. The control unit 70 may restore an internal conductivity and permittivity image, that is, an impedance image, of the measurement target part of the subject H based on measurement values obtained using a plurality of measurement protocols or combination thereof and an enhanced sensitivity matrix of the 3D modeling image I that is generated through the first measurement unit 50.

Figure 6:
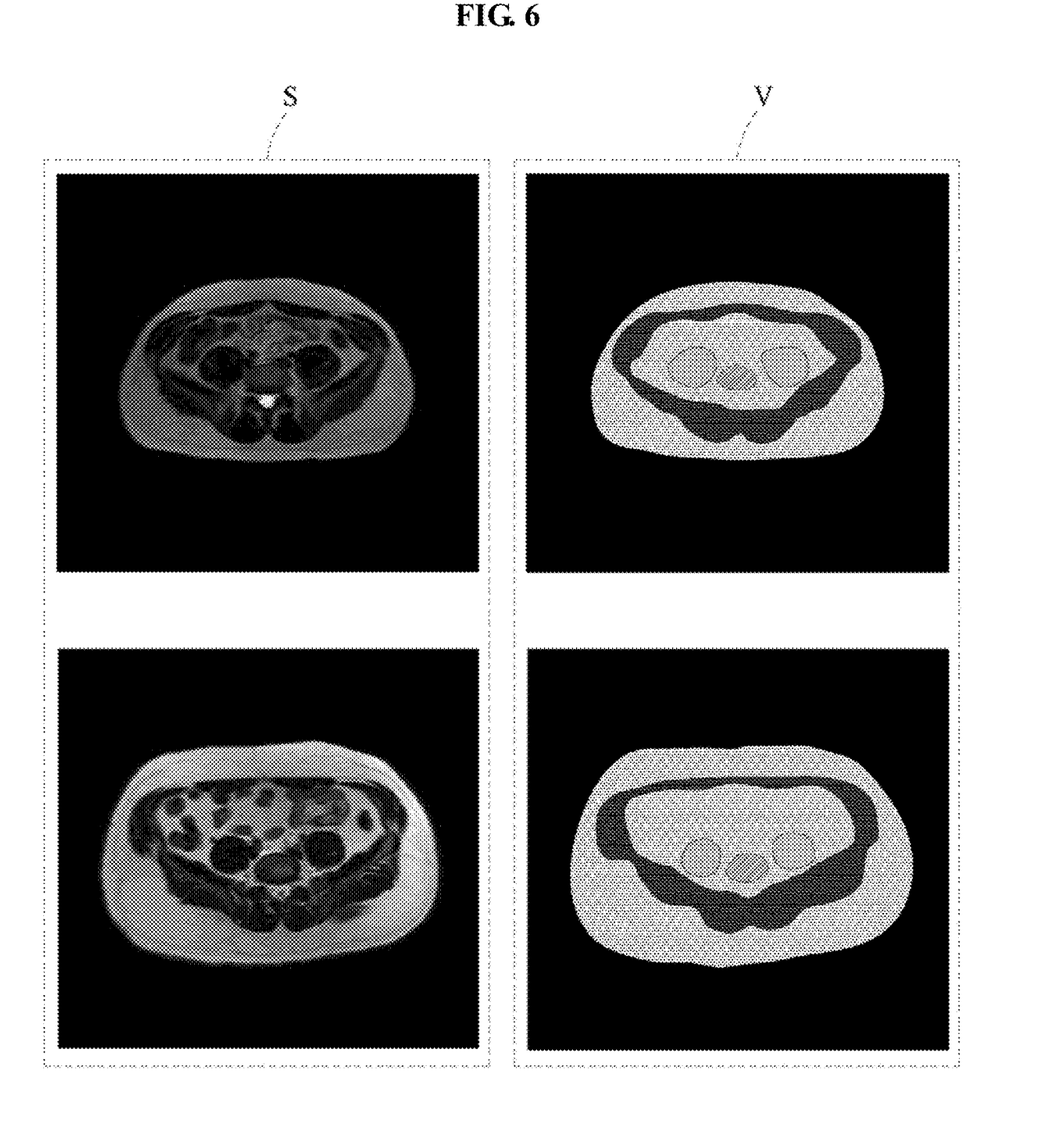
FIG. 6 illustrates an example of an impedance image in which subcutaneous fat and visceral fat are distinguished from each other.

Referring to FIG. 6, a subcutaneous fat (S) area and a visceral fat (V) area around the abdomen that is the measurement target part of the subject H are distinguished from the restored impedance image based on a change trend for each area of location-based conductivity and permittivity information. Here, additional information associated with a boundary between subcutaneous fat and visceral fat may be utilized based on a sensitivity difference for each area from combination of measurement protocols and conductivity and permittivity spectrums.

Figure 7:
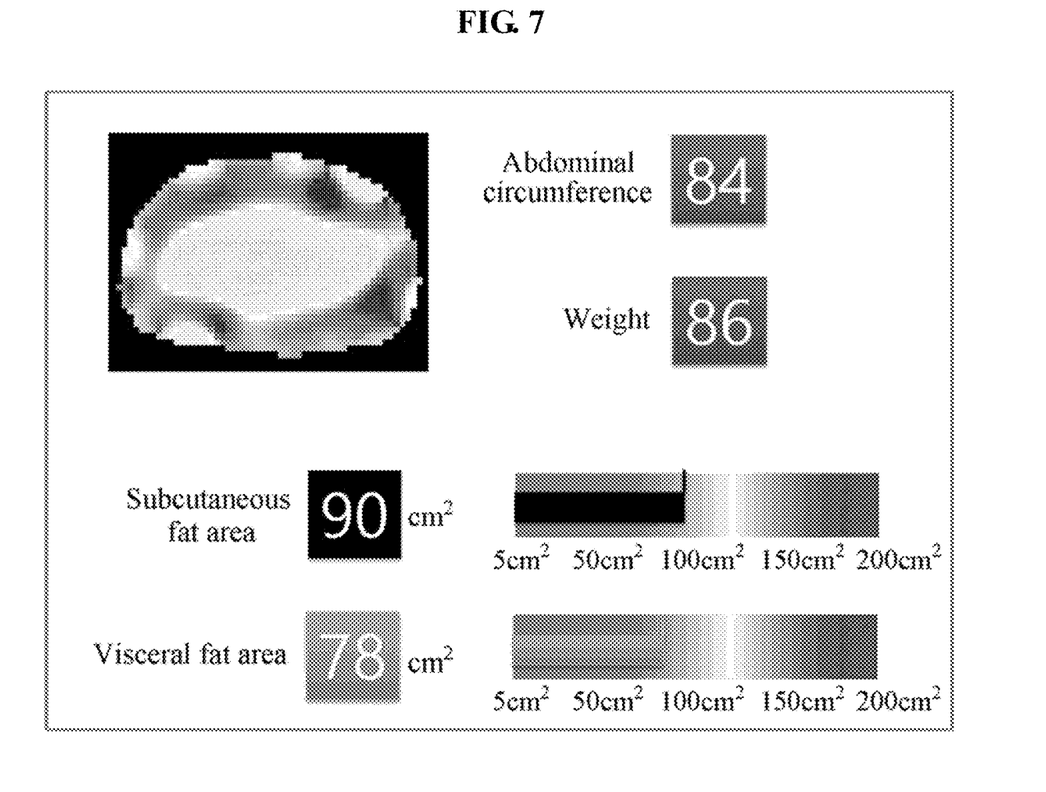
FIG. 7 illustrates an example of outputting information associated with subcutaneous fat and visceral fat.

The control unit 70 may process the restored impedance image and may calculates an amount of subcutaneous fat and an amount of visceral fat. The conductivity and permittivity images with the calculated amount of subcutaneous fat and amount of visceral fat may be output as shown in FIG. 7. Here, referring to FIG. 7, the control unit 70 outputs body type information, for example, a cross-sectional area, a volume, and a weight of the subject H and index information that is proportional to an amount of subcutaneous fat and an amount of visceral fat.

Hereinafter, a body fat measuring method of the body fat measurement apparatus 1 constructed as above is described with reference to FIG. 8. Here, a description is made based on an example in which the body fat measurement apparatus 1 measures body fat of abdomen of the subject H.

Figure 8:
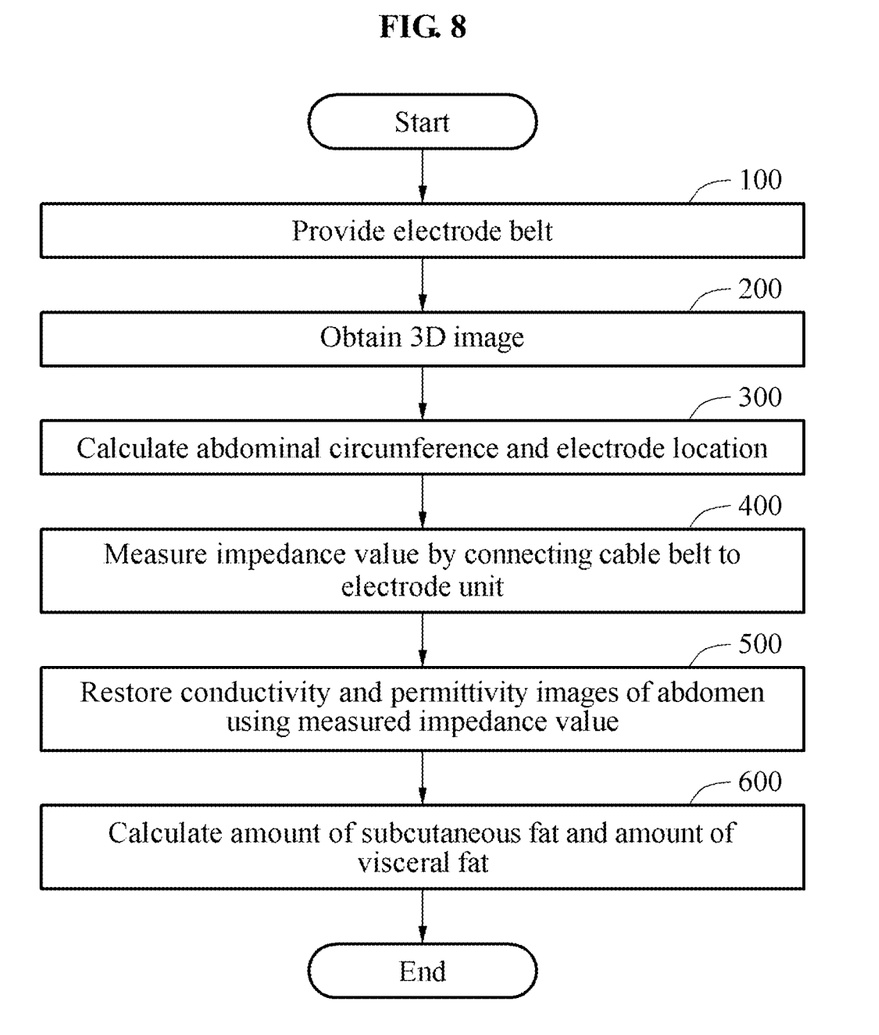
FIG. 8 is a flowchart illustrating a method of measuring body fat according to an example embodiment.

Referring to FIG. 8, in operation 100, the electrode belt 30 of the electrode unit 10 is provided around the abdomen that is the measurement target part of the subject H to be measured. The subject H stands on the rotator 53 with wearing the electrode belt 30 as illustrated in FIG. 1.

The photographing unit 51 rotates as illustrated in FIG. 5A or the rotator 53 on which the subject H stands rotates as illustrated in FIG. 5B. In operation 200, the photographing unit 51 of the first measurement unit 50 takes a photo of the abdomen of the subject H.

Once the 3D image I for the abdomen of the subject H is obtained by the photographing unit 51, the abdominal circumference and a location of the selected composite electrode 20 are calculated by the control unit 70 in operation 300. In operation 400, the impedance measurer 62 measures an impedance value through the selected composite electrode 20 by connecting the cable belt 61 of the second measurement unit 60 to the composite electrode 20 and by injecting current into the composite electrode 20 as illustrated in FIG. 2.

In operation 500, the control unit 70 restores the conductivity and permittivity images of the abdomen using the impedance value measured through the second measurement unit 60 as illustrated in FIG. 6. In operation 600, the control unit 70 separately calculates an amount of subcutaneous fat and an amount of visceral fat based on the restored conductivity and permittivity image and outputs a final image as illustrated in FIG. 7.

Although example embodiments are described, one of ordinary skill in the art may understand that various modifications and changes may be made without departing from the spirit and scope of the disclosure disclosed in the claims.

What is claimed is:

1. A body fat measurement apparatus comprising:
   an electrode unit having a plurality of electrodes and configured to be attachable or wearable around a body of a subject to be measured;
   a first measurement unit configured to obtain a three-dimensional (3D) image for a measurement target part of the subject by taking photos of the electrode until, and configured to detect location information for the plurality of electrodes on the obtained 3D image;
   a second measurement unit configured to measure an impedance value by injecting current into the plurality of electrodes; and a control unit configured to restore at least one conductivity and permittivity image of the subject using the location information for the plurality of electrodes on the 3D image and the impedance value measured from voltage induced by the injected current, and wherein the control unit is further configured to separately calculate an amount of subcutaneous fat and an amount of visceral fat, wherein the amount of subcutaneous fat and the amount of visceral fat are distinguished from each other using the detected location information for the plurality of electrodes and the at least one restored conductivity and permittivity image corresponding to at least one measurement protocol of injecting current into the plurality of electrodes and measuring voltage induced by the injected current.

2. The body fat measurement apparatus of claim 1, wherein the plurality of electrodes are configured to include at least one of a simple electrode and a composite electrode, and the electrode unit comprises an electrode belt having a plurality of electrode installation holes at which the plurality of electrodes are installed, respectively, and made of elastic material.

3. The body fat measurement apparatus of claim 2, wherein the electrode belt is configured to comprise a contact surface on which the plurality of electrodes are installed and configured to contact with the subject, and an exposed surface to face the contact surface and exposed toward the first measurement unit, and wherein the exposed surface comprises a plurality of markers formed using a plurality of colors and patterns which correspond to the plurality of electrodes, respectively.

4. The body fat measurement apparatus of claim 3, wherein the first measurement unit comprises:
   a photographing unit configured to obtain the 3D image by taking a photo of the plurality of markers of the electrode unit mounted to the subject;
   a photographing support configured to ascend or descend while supporting the photographing unit or to be rotatable based on the subject; and
   a rotator configured to be rotatable while supporting the subject and to adjust a distance between the photographing unit and the subject.

5. The body fat measurement apparatus of claim 4, wherein the second measurement unit comprises:
   a cable belt configured to connect to the plurality of electrodes; and
   an impedance measurer configured to measure voltage induced by the current injected into the plurality of electrodes and to transmit the measured voltage to the control unit through the cable belt.

6. The body fat measurement apparatus of claim 5, wherein the control unit is configured to calculate a circumference of the measurement target part of the subject and a location of a selected electrode in response to completion of the 3D image for the measurement target part of the subject using the first measurement unit.

* * * * *